US006551341B2

(12) United States Patent
Boylan et al.

(10) Patent No.: US 6,551,341 B2
(45) Date of Patent: Apr. 22, 2003

(54) DEVICES CONFIGURED FROM STRAIN HARDENED NI TI TUBING

(75) Inventors: John F. Boylan, Murrieta, CA (US);
William J. Boyle, Fallbrook, CA (US);
John E. Papp, Temecula, CA (US);
Anuja H. Patel, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 54 days.

(21) Appl. No.: 09/882,930

(22) Filed: Jun. 14, 2001

(65) Prior Publication Data

US 2002/0193824 A1 Dec. 19, 2002

(51) Int. Cl.$^7$ .............................................. A61M 29/00
(52) U.S. Cl. ...................................................... 606/200
(58) Field of Search ................................ 606/200, 108, 606/194; 420/446, 441, 451

(56) References Cited

U.S. PATENT DOCUMENTS

| 4,505,767 A | 3/1985 | Quin |
| 4,580,568 A | 4/1986 | Gianturco |
| 4,665,906 A | 5/1987 | Jervis |

(List continued on next page.)

FOREIGN PATENT DOCUMENTS

| EP | 0 804 934 A2 | 11/1997 |
| WO | WO 89/12175 | 12/1989 |
| WO | WO 02/36841 A2 | 5/2002 |

OTHER PUBLICATIONS

Duerig, T.W. et al., Linear Superelasticity in Cold–Worked Ni–Ti, *Engineering Aspects of Shape Memory Alloys*, pp. 414–419 (1990).

Duerig, T.W. et al., Ti–Ni Shape Memory Alloys, Materials Properties Handbook Titanium Alloys, *Advanced Materials*, pp. 1035–1048, ASM International (1994).

Schetky, L. McDonald, Shape Memory Alloys, *Scientific American*, pp. 74–82 (Nov. 1979).

Scott M. Russell et al., Improved NiTi Alloys For Medical Applications, *Proceedings of the Second International Conference on Shape Memory and Superelastic Technologies*, pp. 429–436 (1997).

Stöockel, D. et al., Legierungen mit Formgedächtnis, *Kontakt & Studium*, vol. 259, pp. 174–187 (1988) (with translation).

Zhang, C.S. et al., Pseudoelasticity of Near–Equiatomic Ni–Ti Shape Memory Alloy, *Proceedings of the First International Conference on Shape Memory and Superelastic Technologies*, pp. 383–388 (1994).

Duerig, T.W. et al., An Engineer's Perspective of Pseudoelasticity, Engineering Aspects of Shape Memory Alloys, pp. 369–393 (1990).

*Primary Examiner*—Ismael Izaguirre
(74) *Attorney, Agent, or Firm*—Fulwider Patton Lee & Utecht, LLP

(57) ABSTRACT

Cold worked nickel-titanium alloys that have linear pseudoelastic behavior without a phase transformation or onset of stress-induced martensite as applied to a medical device having a strut formed body deployed from a sheath is disclosed. In one application, an embolic protection device that employs a linear pseudoelastic nitinol self-expanding strut assembly with a small profile delivery system for use with interventional procedures is disclosed. Linear pseudoelastic nitinol is used in the medical device as distinct from non-linear pseudoelastic (i.e., superelastic) nitinol. The expandable strut assembly is made from a small diameter tubing of cold worked nickel-titanium alloys. The self-expanding struts that deploy the filter element is laser cut from a large diameter cold worked nickel-titanium alloy, then joined to the small diameter tubing.

21 Claims, 4 Drawing Sheets

U.S. PATENT DOCUMENTS

| | | |
|---|---|---|
| 4,856,516 A | 8/1989 | Hillstead |
| 4,881,981 A | 11/1989 | Thoma et al. |
| 4,925,445 A | 5/1990 | Sakamoto et al. |
| 5,067,957 A | 11/1991 | Jervis |
| 5,092,877 A | 3/1992 | Pinchuk |
| 5,190,546 A | 3/1993 | Jervis |
| 5,234,458 A * | 8/1993 | Metais .......................... 606/1 |
| 5,238,004 A | 8/1993 | Sahatjian et al. |
| 5,292,331 A | 3/1994 | Boneau |
| 5,341,815 A | 8/1994 | Cofone et al. |
| 5,458,615 A | 10/1995 | Klemm et al. |
| 5,486,183 A | 1/1996 | Middleman et al. |
| 5,509,923 A | 4/1996 | Middleman et al. |
| 5,514,154 A | 5/1996 | Lau et al. |
| 5,562,641 A | 10/1996 | Flomenblit et al. |
| 5,569,295 A | 10/1996 | Lam |
| 5,597,378 A | 1/1997 | Jervis |
| 5,632,746 A | 5/1997 | Middleman et al. |
| 5,637,089 A | 6/1997 | Abrams et al. |
| 5,643,312 A | 7/1997 | Fischell et al. |
| 5,720,754 A | 2/1998 | Middleman et al. |
| 5,810,874 A * | 9/1998 | Lefebvre .................... 128/899 |
| 5,843,244 A | 12/1998 | Pelton et al. |
| 5,876,434 A | 3/1999 | Flomenblit et al. |
| 5,885,381 A | 3/1999 | Mitose et al. |
| 5,907,893 A | 6/1999 | Zadno-Azizi et al. |
| 5,927,345 A | 7/1999 | Samson |
| 6,004,330 A | 12/1999 | Middleman et al. |
| 6,051,021 A | 4/2000 | Frid |
| 6,059,810 A | 5/2000 | Brown et al. |
| 6,086,610 A | 7/2000 | Duerig et al. |
| 6,099,549 A * | 8/2000 | Bosma et al. ................ 606/191 |
| 6,106,642 A | 8/2000 | DiCarlo et al. |
| 6,152,946 A | 11/2000 | Broome et al. |
| 6,277,139 B1 * | 8/2001 | Levinson et al. ............ 606/127 |

* cited by examiner

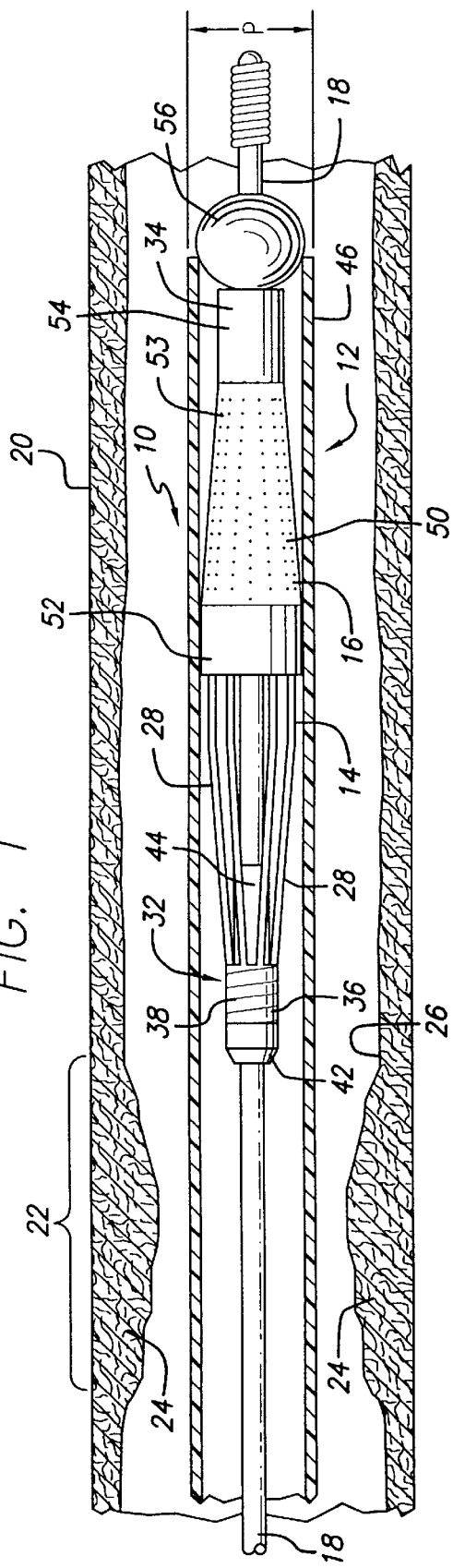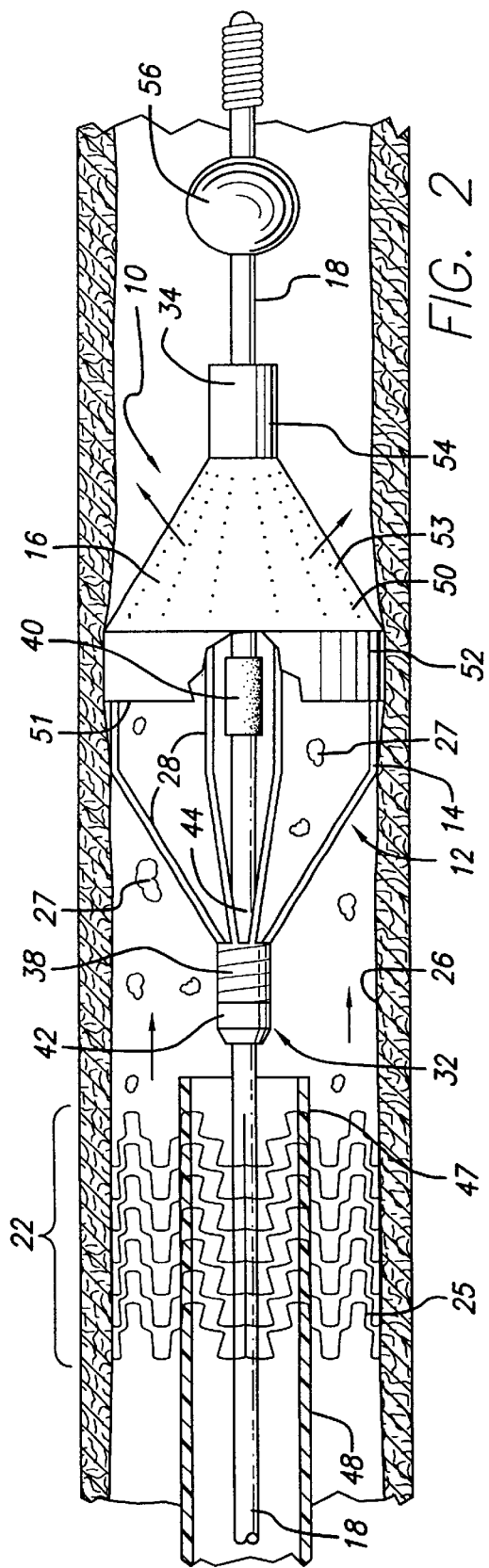

DEVICES CONFIGURED FROM STRAIN HARDENED NI TI TUBING

BACKGROUND OF THE INVENTION

The present invention relates generally to application of nickel-titanium alloys to medical devices. More precisely, the present invention is directed to cold worked nickel-titanium alloys that have pseudoelastic behavior without a phase transformation or onset of stress-induced martensite as applied to a medical device deployed from a sheath.

Near equi-atomic binary nickel-titanium alloys (nitinol) are known to exhibit "pseudoelastic" behavior when given certain cold working processes or cold working and heat treatment processes following hot working. Generally speaking, "pseudoelasticity" is the capacity of the nickel-titanium alloy to undergo large elastic strains on the order of 8 percent or more when stressed and to substantially fully recover all strain upon removal of the stress. Substantially full recovery is typically understood to be less than 0.5 percent unrecovered strain, also known as permanent set or amnesia.

Pseudoelasticity can be further divided into two subcategories: "linear" pseudoelasticity and "non-linear" pseudoelasticity. "Non-linear" pseudoelasticity is sometimes used by those in the industry synonymously with "superelasticity."

Linear pseudoelasticity results from cold working only. Non-linear pseudoelasticity results from cold working and subsequent heat treatment. Non-linear pseudoelasticity, in its idealized state, exhibits a relatively flat loading plateau in which a large amount of recoverable strain is possible with very little increase in stress. This flat plateau can be seen in the stress-strain hysteresis curve of the alloy. Linear pseudoelasticity exhibits no such flat plateau. Non-linear pseudoelasticity is known to occur due to a reversible phase transformation from austenite to martensite, the latter more precisely called "stress-induced martensite" (SIM). Linear pseudoelasticity has no such phase transformation associated with it. Further discussions of linear pseudoelasticity can be found in, for example, T. W. Duerig, et al., "Linear Superelasticity in Cold-Worked Ni—Ti," *Engineering aspects of Shape Memory Alloys*, pp.414–19 (1990).

Because of the useful nature of the nickel-titanium alloy, some have attempted to change its properties to solve different design needs. For example, U.S. Pat. No. 6,106,642 to DiCarlo et al. discloses annealing nitinol to achieve improved ductility and other mechanical properties. U.S. Pat. No. 5,876,434 to Flomenblit et al. teaches annealing and deforming nitinol alloy to obtain different stress-strain relationships.

Binary nickel-titanium alloys have been used in the medical field. Many medical device related applications exploit the non-linear pseudoelastic capabilities of nitinol. Examples include: U.S. Pat. Nos. 4,665,906; 5,067,957; 5,190,546; and 5,597,378 to Jervis; and U.S. Pat. Nos. 5,509,923; 5,486,183; 5,632,746; 5,720,754; and 6,004,629 to Middleman, et al.

Yet another application of nickel-titanium alloys is in an embolic protection or filtering device. Such embolic filtering devices and systems are particularly useful when performing balloon angioplasty, stenting procedures, laser angioplasty, or atherectomy in critical vessels, particularly in vessels such as the carotid arteries, where the release of embolic debris into the bloodstream can occlude the flow of oxygenated blood to the brain or other vital organs. Such an occlusion can cause devastating consequences to the patient. While the embolic protection devices and systems are particularly useful in carotid procedures, they are equally useful in conjunction with any vascular interventional procedure in which there is an embolic risk. An embolic protection device that uses superelastic nitinol recently released to the market by the Cordis Corporation is known as the ANGIOGUARD.

What has been needed and heretofore unavailable in the prior art is a medical device that exploits the benefits of linear pseudoelastic nitinol. With the use of linear pseudoelastic nitinol, the mechanical strength of the device is substantially greater per unit strain than a comparable device made of superelastic nitinol. Furthermore, smaller component parts such as struts can be used because of the greater storage of energy available in a linear pseudoelastic nitinol device.

SUMMARY OF THE INVENTION

The present invention is generally directed to cold worked nickel-titanium alloys that have linear pseudoelastic behavior without a phase transformation or onset of stress-induced martensite as applied to a medical device having a strut formed body deployed from a sheath.

In one preferred embodiment, the present invention is directed to a medical device for use in a body lumen comprising a body formed from struts, wherein the body includes a cold formed nickel-titanium alloy, and the nickel-titanium alloy is in a martensitic phase when the body is stressed into a first shape and also when the stress to the body is relieved to assume a second shape. The present invention further includes a sheath at least partially enveloping the body in its first shape. The sheath may be used to transport the device to a targeted location in the patient's anatomy, to deploy the device, and to retrieve the device at the end of the procedure.

The raw nitinol for use in the present invention has been cold formed and is further cold worked to set the desired expanded shape. Furthermore, the cold forming and cold working occur below the recrystallization temperature of the nitinol alloy.

During its operation, the linear pseudoelastic nitinol device can be stressed without developing stress-induced martensite in the alloy. Consistent with this behavior, an idealized stress-strain curve of the linear pseudoelastic nitinol does not contain any flat stress plateaus. Furthermore, despite application of stress, the nitinol alloy does not undergo a phase transformation from austenite to martensite or vice versa.

The resulting preferred embodiment device has greater mechanical strength at any given strain as compared to a device made of a standard superelastic nitinol. The stress-strain curve of the present invention linear pseudoelastic nitinol device also possesses more energy storage capacity. As a result, for a given desired performance requirement, the present invention linear pseudoelastic nitinol device allows for smaller struts and consequently a lower profile useful in crossing narrow lesions.

Another advantage is that because the present invention uses linear pseudoelastic nitinol, the underlying alloy can be selected from a broader range of available materials yet still maintain consistent, mechanical properties. In other words, there is less sensitivity to material variations and processing vagaries as compared to superelastic nitinol. In addition, since the linear pseudoelastic nitinol has no transformation from martensite to austenite or vice versa, there is less of an influence by temperature-related effects.

There are many specific applications for the present invention including vena cava filters, septal plugs, just to name a few. One specific application for the present invention is in a filtering device and system for capturing embolic debris in a blood vessel created during the performance of a therapeutic interventional procedure, such as a balloon angioplasty or stenting procedure, in order to prevent the embolic debris from blocking blood vessels downstream from the interventional site. The devices and systems of the present invention are particularly useful while performing an interventional procedure in critical arteries, such as the carotid arteries, in which vital downstream blood vessels can easily become blocked with embolic debris, including the main blood vessels leading to the brain. When used in carotid procedures, the present invention minimizes the potential for a stroke occurring during the procedure. As a result, the present invention provides the physician with a higher degree of confidence that embolic debris is being properly collected and removed from the patient's vasculature during the interventional procedure.

An embolic protection device and system made in accordance with the present invention preferably includes an expandable filter assembly which is affixed to the distal end of a cylindrical shaft, such as a guide wire. The filter assembly includes an expandable strut assembly preferably made from a linear pseudoelastic nitinol, and includes a number of outwardly biased and extending struts that are capable of self-expansion from a contracted or collapsed position to an expanded or deployed position within a patient's vasculature. A filter element made from an embolic capturing media is attached to the expandable strut assembly. The filter element opens from a collapsed configuration to an expanded configuration via the movement of the expandable struts similar to that of an umbrella.

The present invention further contemplates a medical device for use in a body lumen comprising a tubular body formed from small diameter tubing, a plurality of struts formed from a large diameter tubing and disposed on the tubular body such that the struts project radially outward in an unstressed state, wherein the large diameter tubing includes a cold formed nickel-titanium alloy, and the nickel-titanium alloy is in a martensitic phase only regardless of stress applied to the alloy, and a sheath at least partially enveloping the body and restraining the struts in a compressed state for delivery and retrieval of the device to and from the body lumen.

With this embodiment, it is no longer necessary to fabricate an expanded strut assembly from a small tubing that is heat treated to the expanded state. Rather, the expanded strut assembly starts out as a large diameter tubing wherein the struts themselves are formed from a large diameter tubing and assembled inward to the desired embolic protection device shape. The struts are preferably laser cut from the large tubing and are joined to the small diameter tubing such that in their unconstrained and stable state, they project radially outward thereby accomplishing the same expanded state without need of heat treatment.

By using a large diameter, cold worked or strain hardened nickel-titanium hypotube in the assembly of the expanded strut assembly, the strain hardened nickel-titanium material has increased mechanical properties that allow for the design of thinner walled interventional devices. Processing the interventional devices from large diameter hypotube allows for greater design flexibility and the ability to create more intricate designs, because of the increased surface area of the large diameter nickel-titanium hypotube. Moreover, a thinner walled device presents a reduced overall crossing profile and further improves system trackability through a tortuous anatomy.

Other features and advantages of the present invention will become more apparent from the following detailed description of the invention when taken in conjunction with the accompanying exemplary drawings.

BRIEF DESCRIPTION OF THE DRAWINGS

FIG. 1 is a side elevational view, partially in cross-section, of an embolic protection device embodying features of the present invention showing the expandable filter assembly in its collapsed position within a restraining sheath and disposed within a vessel.

FIG. 2 is a side elevational view, partially in cross-section, similar to that shown in FIG. 1, wherein the expandable filter assembly is in its expanded position within the vessel.

FIG. 6c is a perspective view of one embodiment of an expandable strut assembly after the struts of FIG. 6b have been joined to the tubular body of FIG. 6a.

DETAILED DESCRIPTION OF THE PREFERRED EMBODIMENTS

Figure 3:
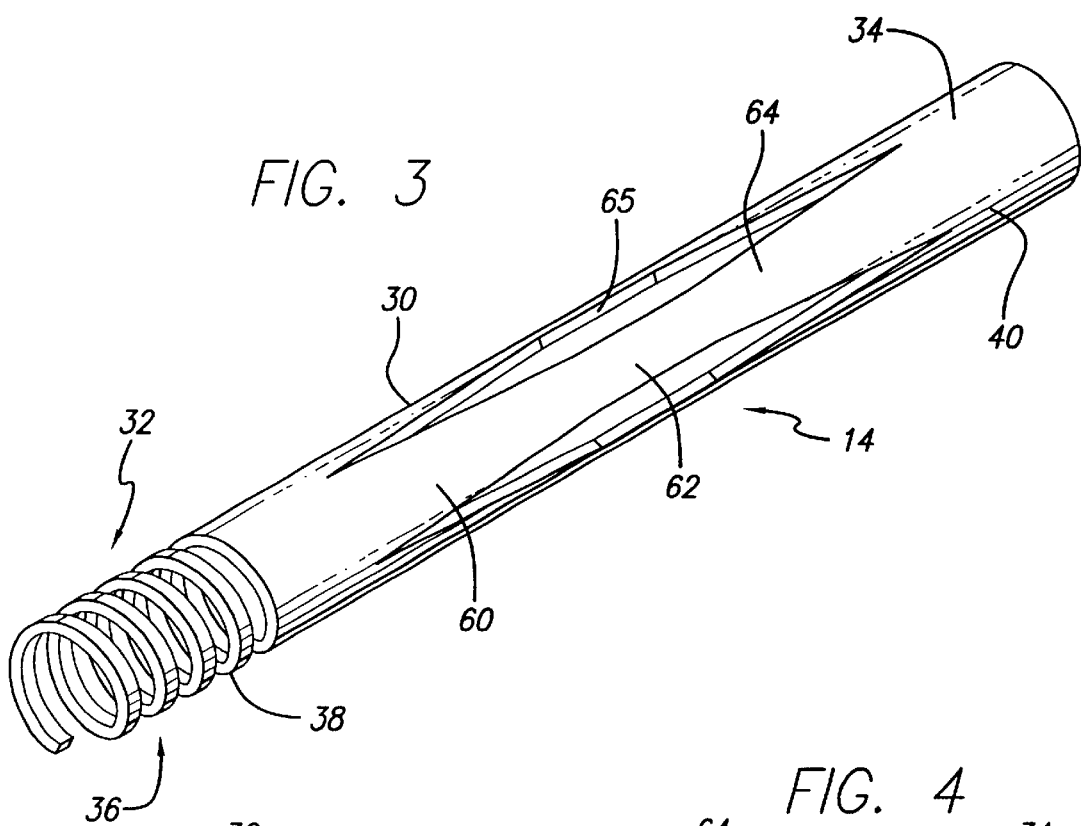
FIG. 3 is a perspective view of an expandable strut assembly which forms part of the filter assembly of the present invention as shown in its collapsed position.

The present invention is generally directed to cold worked nickel-titanium alloys that have linear pseudoelastic behavior without a phase transformation or onset of stress-induced martensite as applied to a medical device having a strut formed body deployed from a sheath. Although the present invention is applicable to and contemplates numerous medical devices, for the sake of illustration, the following detail description focuses on an exemplary embodiment involving a filtering device and system for capturing embolic debris in a blood vessel created during the performance of a therapeutic interventional procedure.

In a preferred embodiment, the present invention medical device has a body formed from struts, wherein the body includes a cold formed nickel-titanium alloy, and the nickel-titanium alloy is in a martensitic phase when the body is stressed into a first shape and also when the stress on the body is relieved to assume a second shape. The preferred embodiment further includes a sheath at least partially enveloping the body in its first shape. The sheath may be used to transport the device to a targeted location in the patient's anatomy, to deploy the device, and to retrieve the device at the end of the procedure.

Turning now to the drawings, in which like reference numerals represent like or corresponding elements, FIGS. 1 and 2 illustrate a preferred embodiment embolic protection device 10 incorporating features of the present invention. In the particular exemplary embodiment shown in FIGS. 1 and 2, the embolic protection device 10 has a body identified as a filter assembly 12, which assembly includes an expandable strut assembly 14 and a filter element 16. The filter assembly 12 is optionally rotatably mounted or fixed on the distal end of an elongated tubular shaft. The shaft as shown in FIGS. 1 and 2 is a guide wire 18, for example.

FIG. 1 also depicts a delivery system having a small delivery profile P. This reduced profile P is an advantage of the present invention filter assembly 14 and delivery system (restraining sheath 46 and recovery sheath 48), and is a result of the stress-strain hysteresis curve for linear pseudoelastic nitinol. This novel approach is described more fully below.

In the side elevational and cross-sectional views of FIGS. 1 and 2, the embolic protection device 10 is positioned within an artery 20 or other lumen of a patient. This portion of the artery 20 has an area of treatment 22 in which atherosclerotic plaque 24 has built up against the inside wall 26 of the artery 20. The filter assembly 12 is placed distal to, and downstream from, the area of treatment 22.

A balloon angioplasty catheter (not shown) can optionally be introduced within the patient's vasculature in a conventional Seldinger technique through a guiding catheter (not shown). The guide wire 18 is passed through the area of treatment 22 and the dilatation catheter can be advanced over the guide wire 18 within the artery 20 until the balloon portion is appositioned directly in the area of treatment 22. The balloon of the dilatation catheter is inflated, thereby expanding the plaque 24 against the inside wall 26 of the artery 20. This opens the occlusion, expands the artery 20, and reduces the blockage in the vessel caused by the plaque 24.

After the dilatation catheter is removed from the patient's vasculature, a stent 25 (shown in FIG. 2) may be delivered to the area of treatment 22 using over-the-wire techniques. The stent 25 helps to scaffold and maintain the area of treatment 22, which in turn help to prevent restenosis from occurring in the area of treatment 22.

Any embolic debris 27 that breaks off from the plaque 24 during the interventional procedure is released into the bloodstream. The embolic debris 27 is carried by blood flow (indicated by arrows) and is captured by the deployed, i.e., unfurled, filter element 16 of the filter assembly 12 located downstream from the area of treatment 22. Once the interventional procedure is completed, the filter assembly 12 is collapsed and removed from the patient's vasculature, taking with it embolic debris 27 trapped within the filter element 16.

One exemplary embodiment of the expandable strut assembly 14 is shown in FIGS. 1–2. As can be seen in these figures, the expandable strut assembly 14 includes a plurality of radially expandable struts 28 that can move from a compressed or collapsed position as shown in FIG. 1 to an expanded or deployed position shown in FIG. 2. The expandable strut assembly 14 is preferably made from a linear pseudoelastic nitinol alloy so that the struts 28 have a radially outward bias toward the expanded position.

The expandable strut assembly 14 includes a proximal end 32 which is optionally rotatably attached to the guide wire 18. A distal end 34 is free to slide longitudinally along the guide wire 18 and can rotate thereabout. The distal end 34 translates along the guide wire 18 whenever the struts 28 move between the expanded and contracted positions. A proximal end 32 includes a short tubular segment or sleeve 36 which has a coil spring formed therein and which acts as a dampening member or element 38. The function of the dampening element 38 is explained below. The distal end 34 of the tubing 30 preferably includes a short segment or sleeve 40 which is slidably and rotatably disposed on the guide wire 18.

The filter element 16 in one preferred embodiment of the invention includes a tapered or cone shaped section 50, as seen in FIGS. 1 and 2. The filter element 16 optionally has a plurality of openings 53 that allow the blood to perfuse through (indicated by arrows), yet the openings 53 are small enough that the embolic debris 27 is captured inside the cone shaped section 50. The filter element 16 includes a short proximal section 52 which is integral with the cone shaped section 50 and expands to a substantially cylindrical shape when the struts 28 of strut assembly 14 are deployed. An inlet opening 51 located at the short proximal section 52 of cone shaped section 50 collects embolic debris 27, directing the debris 27 into the filter element 16.

The short proximal section 52 also functions as a superstructure to which the filter element 16 and the struts 28 of the strut assembly 14 can be adhesively or otherwise affixed. At the opposite end, the filter element 16 has a short distal cylindrical section 54 which is integral with the remaining sections of the filter element and is attached to the distal end 34 of the expandable strut assembly 14.

As best seen in FIG. 1, the filter assembly 12 is maintained in its collapsed or compressed position through the use of a restraining sheath 46. The restraining sheath 46 should have sufficient elasticity to resist the outward bias of the struts 28. One manner of achieving the required elasticity is through selection of the proper size and wall thickness for the sheath 46. Another is through use of the proper elastic material that has sufficient resilience to resist the expansive forces of the struts 28 held therein. Such sheath materials and designs are known in the art.

The guide wire 18 and the restraining sheath 46 have proximal ends (not shown) that extend outside of the patient. From outside the patient, it is possible to manipulate the struts 28 into the expanded position by retracting the restraining sheath 46 via its proximal end to expose the struts 28. Since the struts 28 are self-expanding by nature, the withdrawal of the restraining sheath 46 allows the struts 28 to spring open and the filter element 16 to unfurl into their expanded positions within the artery 20. This is depicted in FIG. 2.

The guide wire 18 optionally includes a small sphere 56 affixed thereto. The small sphere 56 is useful during the delivery of the embolic protection device 10 into the patient's vasculature. Specifically, the sphere 56 is approximately as large as the inner diameter of the restraining sheath 46 and is effectively used as a nose cone. The nose cone prevents possible "snowplowing" of the embolic protection device 10 as it is delivered through the patient's arteries.

When the embolic protection device 10 is to be removed from the patient's vasculature, an optional recovery sheath 48 is used to collapse and recover the filter assembly 12, as shown in FIG. 2. Generally, this recovery sheath 48 has a slightly larger inner diameter than the restraining sheath 46 since the struts 28 are now deployed. Furthermore, the recovery sheath 48 must have sufficient tensile strength and elasticity at the distal end 47 to be capable of collapsing the expanded strut assembly 14.

The collapse of the expandable strut assembly 14 can be accomplished by holding the guide wire 18 and moving the proximal end (not shown) of the recovery sheath 48 forward, which moves the distal end 47 of the sheath 48 over the struts 28. Alternatively, the recovery sheath .48 can be held stationary while the proximal end of the guide wire 18 is retracted back to pull the entire filter assembly 12 into the sheath 48. Upon collapse of the filter assembly 12, any embolic debris 27 generated and entering the bloodstream during the interventional procedure remains trapped inside the filter element 16 and is withdrawn from the bloodstream when the embolic protection device 10 is removed from the patient's vasculature.

The number of struts 28 formed on the expandable strut assembly 14 can be any number which provides sufficient expandability within the artery to properly deploy and maintain the filter element 16 in place. In the embodiment shown in FIGS. 1 and 2, the expandable strut assembly has four self-expanding struts 28. Likewise, the particular size and shape of each strut 28 can be varied.

Figure 4:
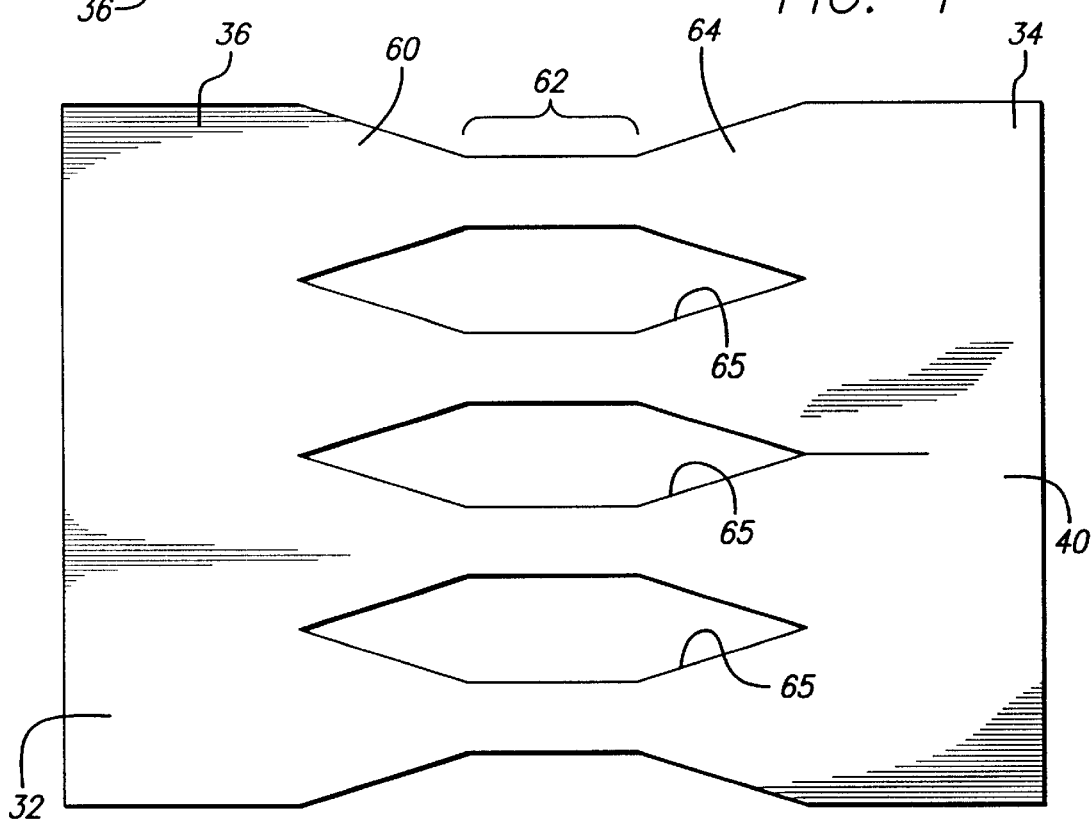
FIG. 4 is a plan view of a flattened section of the expandable strut assembly shown in FIG. 3 which illustrates one particular strut pattern.

FIGS. 3–4 show an expandable strut assembly 14 having a strut pattern formed from an inverted, triangular shape first portion 60, a substantially straight center section 62, and a second inverted triangular shaped section 64, which completes the strut. This particular strut pattern is one preferred design that provides greater strength in regions of the strut where there would be a tendency for the strut to break or become weakened. These regions include the very proximal and distal ends of each strut which are designed with a wider base. This particular design also allows the expandable strut assembly 14 to open and close more uniformly. This is advantageous especially when collapsing the struts for removal from the patient. Additionally, the center section 62 allows the struts 28 to expand to a greater volume, which allows a larger filter element to be placed on the strut assembly 14, if needed.

When the precise pattern is cut into the tubing 30, a sleeve 36 which forms the proximal end 32 may optionally be formed into a helical coil as shown in FIG. 3. The helical coil then functions as a damping element 38 for the expandable strut assembly 14. As seen in FIGS. 1 and 2, the sleeve 36 slides over the guide wire 18. The proximal end 32 of the expandable strut assembly 14 is mounted between a tapered fitting 42 and an optional radiopaque marker band 44. The tapered end fitting 42 and the marker band 44 affix the proximal end 32 on to the guide wire 18 to prevent any longitudinal motion, yet allow for rotation of the filter assembly 12.

FIG. 4 is a plan view of a rolled out flat sheet of the tubing 30 used to form the struts 28. Preferably, however, the tubing 30 is made from nitinol and the initial state of the tubing is cold worked and fully martensitic in the as-received condition. A particular design pattern is cut into the thin wall of the tubing 30 in order to form each strut. In the case of the exemplary embodiment shown in FIG. 3, that pattern consists of truncated diamond shape apertures 65 which help form the first section 60, the center section 62 and the triangular shaped section 64. To create the apertures 65, portions of the tubing 30 are selectively removed through laser cutting preferably, but etching, stamping, or other processes are suitable insofar as each particular strut can be fashioned into a precise shape, width, and length. This truncated diamond aperture pattern 65 repeats, as seen in FIG. 4, to provide uniform size to each of the struts 28 formed therein. Narrow struts such as that shown in FIGS. 1 and 2 can, of course, be formed as described above.

Subsequently, the laser cut nitinol tubing 30 is preferably cold formed and specifically cold worked with no heat treatment such that it remains in the fully martensitic state. The cold working proceeds only at temperatures below the recrystallization temperature of the nitinol alloy. Next, the laser-cut nitinol tubing 30 is cold worked to its desired expanded size. The desired expanded size is thus imparted or set into the laser cut tube.

Alternatively, the tube can be swagged and drawn into the desired shape and size. Also, the tubing itself may be formed from nitinol sheet stock rolled into a tube and joined at the seam, then cold drawn to the desired size. The tube is then laser cut and processed to ensure that the material remains in a fully martensitic state.

Importantly, the laser-cut nitinol tubing 30 is not heat treated to prevent generation of any loading or unloading plateaus in the stress-strain curve. In an alternative embodiment, the nitinol tubing may undergo heat treating for only very limited durations at low temperatures. The present invention recognizes that a significant difference between linear pseudoelasticity and non-linear pseudoelasticity is the absence or presence, respectively, of stress-induced martensite. It also recognizes that in order to set a particular shape in nitinol, the nitinol must be heat treated at a relatively high temperature for a short period of time. Under normal circumstances, this material would then exhibit non-linear pseudoelasticity and therefore would undergo a reversible phase transformation from austenite to martensite. When setting a shape under standard conditions, for example, 550 degrees C for 5 minutes, the nitinol exhibits essentially no springback; that is, its unconstrained shape after heat treatment is nearly identical to its constrained shape during heat treatment. The nitinol does not spring back to its original shape prior to heat treatment. At the other extreme, linear pseudoelastic nitinol with no heat treatment has 100 percent springback and always returns to its original, cold worked shape.

Springback is a continuous function between no heat treatment (100 percent springback) and ideal shape setting heat treatment (approximately zero percent springback). From an engineering perspective for design of nitinol based pseudoelastic devices, less springback is more favorable than more springback. However, in some circumstances, linear pseudoelasticity may be preferable to non-linear pseudoelasticity. Therefore, the present invention, in addition to contemplating cold-worked only nitinol, addresses that regime of heat treatment temperatures and times within which springback is adequately minimized to successfully impart a desired shape to the nitinol structure and within which the nitinol does not develop a stable and reversible martensitic phase.

In the preferred embodiment of the present invention, to achieve the linear pseudoelastic behavior, the binary nickel-titanium tubing has approximately 55.8 atomic percent nickel. The tubing must contain a minimum of approximately 38 percent cold working when measured by the reduction in cross-sectional area, and there is not to be any heat treatment following final cold reduction. As to the alternative embodiment, the present invention contemplates accumulated heat treatment of the tubing of up to 300 degrees C for up to 5 minutes. Under ideal conditions, these process parameters should adequately ensure that the nitinol remains martensitic without a phase change under stress.

Figure 5:
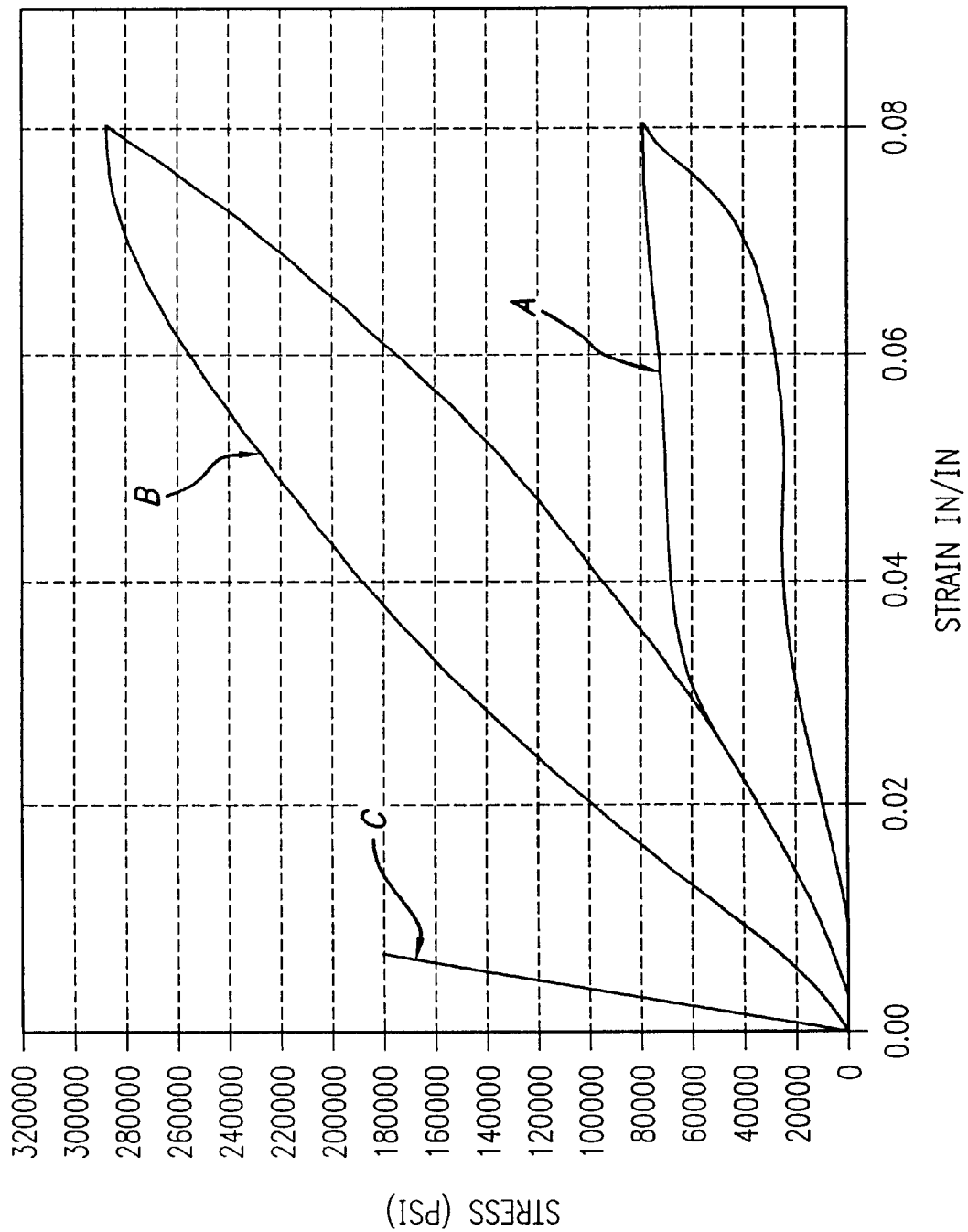
FIG. 5 is a set of stress-strain curves for conventional 316L stainless steel, linear pseudoelastic nitinol, and non-linear pseudoelastic nitinol.

To illustrate the metallurgical aspects of cold worked nickel-titanium alloys, FIG. 5 contains the elastic component of three idealized stress-strain curves for 316L stainless steel, linear pseudoelastic nitinol, and non-linear pseudoelastic nitinol. In a preferred embodiment, the expandable strut assembly 14 of the present invention is formed partially or completely of alloys such as the linear pseudoelastic nitinol shown in FIG. 5.

In FIG. 5, in an idealized curve A for a non-linear pseudoelastic nitinol, the relationship is plotted on x-y axes, with the x axis representing strain and the y axis representing stress. The x and y axes are labeled in units of stress from zero to 320 ksi and strain from 0 to 9 percent, respectively.

In curve A, when stress is applied to a specimen of a metal such as nitinol exhibiting non-linear pseudoelastic characteristics at a temperature at or above that which the transformation of the martensitic phase to the austenitic phase is complete, the specimen deforms elastically until it reaches a particular stress level where the alloy then undergoes a stress-induced phase transformation from the austenitic phase to the martensitic phase (i.e., the stress-induced martensite phase). As the phase transformation progresses, the alloy undergoes significant increases in strain with little or no corresponding increases in stress. On curve A this is represented by upper, nearly flat stress plateau at approximately 70 to 80 ksi. The strain increases while the stress remains essentially constant until the transformation of the austenitic phase to the martensitic phase is complete. Thereafter, further increase in stress is necessary to cause further deformation. The martensitic metal first yields elastically upon the application of additional stress and then plastically with permanent residual deformation (not shown).

If the load on the specimen is removed before any permanent deformation has occurred, the martensite specimen elastically recovers and transforms back to the austenitic phase. The reduction in stress first causes a decrease in strain. As stress reduction reaches the level at which the martensitic phase transforms back into the austenitic phase, the stress level in the specimen remains essentially constant (but less than the constant stress level at which the austenitic crystalline structure transforms to the martensitic crystalline structure until the transformation back to the austenitic phase is complete); i.e., there is significant recovery in strain with only negligible corresponding stress reduction. This is represented in curve A by the lower stress plateau at about 20 ksi.

After the transformation back to austenite is complete, further stress reduction results in elastic strain reduction. This ability to incur significant strain at relatively constant stress upon the application of a load and to recover from the deformation upon the removal of the load is commonly referred to as non-linear pseudoelasticity (or superelasticity).

FIG. 5 also has a curve B representing the idealized behavior of linear pseudoelastic nitinol as utilized in the present invention. Curve B generally has a higher slope or Young's Modulus than curve A for the non-linear pseudoelastic nitinol. Also, curve B does not contain any flat plateau stresses found in curve A. This stands to reason since the nitinol of curve B remains in the martensitic phase throughout and does not undergo any phase change. The same tension and release of stress cycle to generate curve A is used to generate curve B. To that end, curve B shows that increasing stress begets a proportional increase in reversible strain, and a release of stress begets a proportional decrease in strain. The areas bounded by curves A and B represent the hysteresis in the nitinol.

As apparent from comparing curve B to curve A in FIG. 5, with the use of linear pseudoelastic nitinol, the mechanical strength of the present invention medical device is substantially greater per unit strain than a comparable device made of superelastic nitinol. Consequently, a major benefit is that smaller component parts such as struts can be used because of the greater storage of energy available in a linear pseudoelastic nitinol device. A small profile is one critical factor for crossing narrow lesions or for accessing remote and tortuous arteries.

FIG. 5 includes curve C which is the elastic behavior of a standard 316L stainless steel. Stress is incrementally applied to the steel and, just prior to the metal deforming plastically, decrementally released. It is provided here simply for comparison to curves A and B.

As mentioned above, the present invention medical device uses preferably a binary nickel-titanium alloy. In an alternative embodiment, however, the nickel-titanium may be alloyed with a ternary element such as palladium, platinum, chromium, iron, cobalt, vanadium, manganese, boron, copper, aluminum, tungsten, tantalum, or zirconium.

FIGS. 6a–6e illustrate a preferred embodiment construction of the expandable strut assembly 14 wherein large diameter strain hardened (i.e., cold worked linearly pseudoelastic) nickel-titanium tubings are used. As mentioned earlier, the use of cold worked nitinol material increases the device's mechanical properties, which allows for the design of thinner walled interventional devices. Also, processing the device from a large diameter hypotube permits greater design flexibility and the ability to create more intricate design options because of the increased surface area of the large diameter nickel-titanium hypotube.

A problem to be resolved was how to construct an expandable strut assembly or basket made from tubing yet avoid heat treating the nickel-titanium alloy. Many designs employ a basket made from small diameter tubing that is heat treated to set the expanded shape. In the present embodiment, the deploying struts are made from a large diameter tubing and attached to a small diameter tubing. A medical device fashioned from this combination of tubing sizes avoids or minimizes the need for heat treating steps.

In various alternative embodiments, the basket shape can be made by swagging from large diameter tubing. Further, a sheet of the nitinol material can be processed into a tube, or the sheet can be formed to create approximately one-half of he desired basket shape.

Figure 6A:
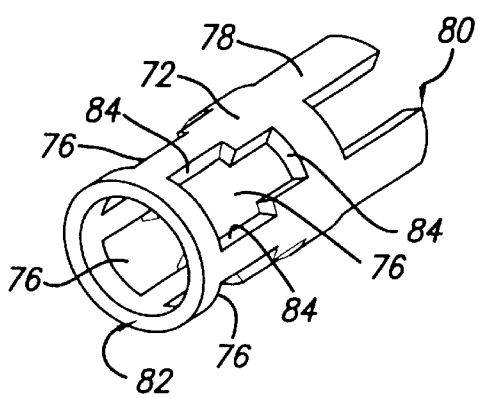
FIG. 6a is a perspective view of a tubular body cut from a small diameter tubing with apertures cut therein.
Figure 6B:
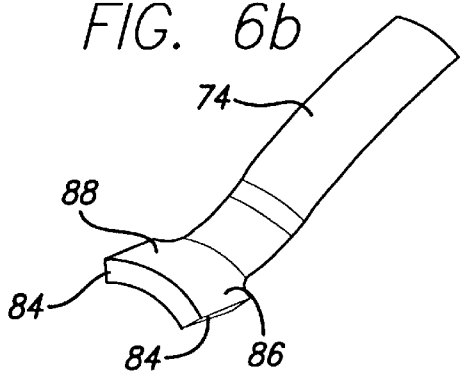
FIG. 6b is a strut formed from a large diameter tubing.
Figure 6C:
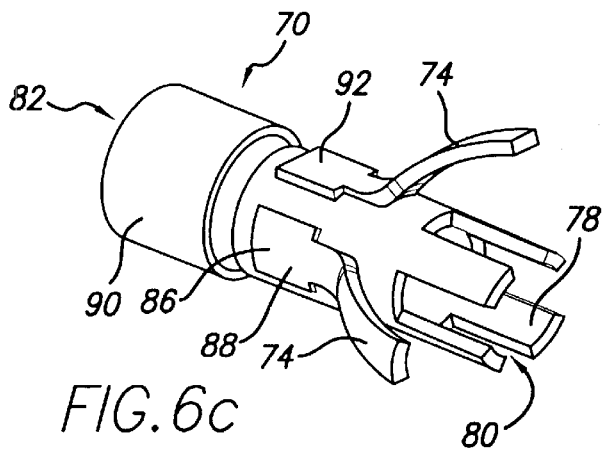
Figure 6D:
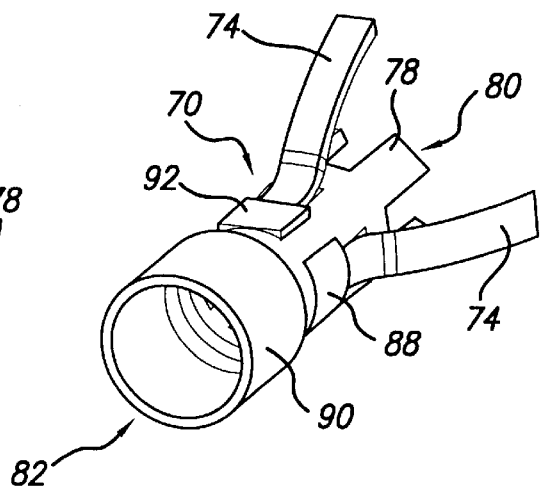
FIG. 6d is a perspective view of the expandable strut assembly of FIG. 6c with the proximal end in the foreground.
Figure 6E:
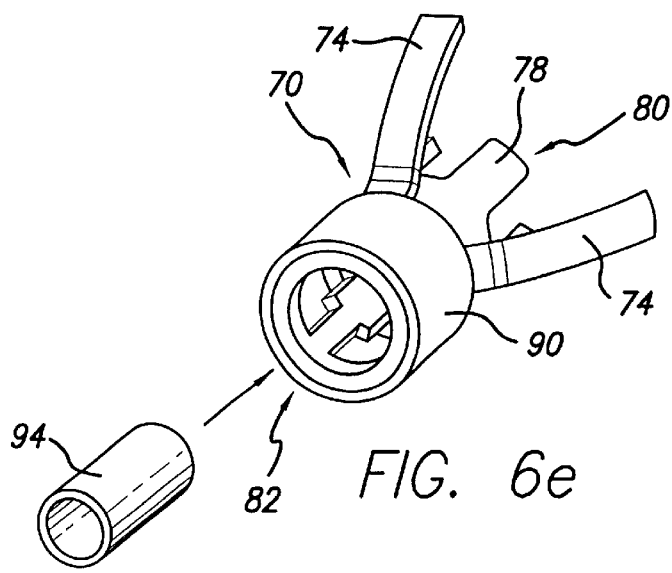
FIG. 6e is a perspective view of the expandable strut assembly of FIGS. 6c and 6d, wherein a retainer sleeve is fully engaged to the body to retain the struts thereto.

FIG. 6e is a perspective view of a preferred embodiment expandable strut assembly 70. The expandable strut assembly 70 is separated into its two major component parts in FIGS. 6a and 6b. FIG. 6a shows a tubular body 72 formed from a small diameter tubing. Comparable sizes include 0.5 to 1.0 mm diameter hypotubes.

FIG. 6b is a perspective view of a strut 74 fashioned from a large diameter tubing. Comparable large diameter tubing can be found in 4 to 50 mm diameter hypotubes. Both the small diameter tubing and the large diameter tubing are preferable made from the aforementioned cold worked nickel-titanium alloy. Other materials known in the art can also be used.

In FIG. 6a, the tubular body 72 has been laser cut through processes known in the art to create a particular shape with apertures or key holes 76 formed therein. The key holes 76 are dispersed around the circumference of the tubular body 72 and there are preferably four key holes. Obviously, depending on design, there can be more or fewer key holes and their locations can be changed depending upon the assembly location of the strut 74 as described in further detail below. The tubular body 72 has a proximal end 82 and a distal end 80. At the distal end 80 there are preferably four tabs 78 to facilitate mounting of the expandable strut assembly 70 to the guide wire 18. Furthermore, the key holes 76 are cut or formed so that they have a bevel 84 along the periphery of the aperture. The bevel 84 along the key hole 76 periphery decreases the opening size towards the interior of the tubular body 72. Thus, when a complementary part is assembly to cover the key hole 76, that part tends to wedge into the beveled opening.

FIG. 6b is a perspective view of a strut 74 that has been preferably laser cut from a large diameter tubing. The strut 74 has a long beam terminating in a wide base 86. Preferably, the wide base 86 has a periphery that also includes a bevel 84 that complements the bevel 84 at the key holes 76. In addition, the wide base 86 is shown with an optional curvature 88. The curvature 88 is intended to match the curvature of the tubular body 72.

FIGS. 6c and 6d are alternative perspective views of the expandable strut assembly 70 showing the distal end 80 and then the proximal end 82 in the foreground, respectively. As seen in either drawing, two struts 74 have been assembled to the tubular body 72 in which the wide base 86 mates with the complementary-shaped key hole 76. Two more struts 74 can be attached to the remaining two key holes 76, but have been omitted from the drawings for the sake of clarity of illustration. As seen in FIGS. 6c and 6d, the struts 74 have a profile in the form of an ogee, wherein the long beam bends outwardly and then bends back toward the tubular body 72. These curves in the struts 74 are preferably formed by cold working after their basic shape has been cut from the large diameter tubing. The curved profile of the struts 74 can of course be changed to suit the design of the expandable strut assembly and spring forces needed to deploy the filter element 16. As distinguished from conventional nitinol material, the present invention strut preferably incorporates the necessary curves in its profile through cold working and not through heat setting. With minimal or no heat treatment, the nickel-titanium alloy has a stress-strain curve similar to that shown in FIG. 5, in which curve B lacks a discernible flat stress plateau. As a result, when the struts 74 are held tightly against the exterior of the tubular body 72 by a delivery sheath or the like, there is no creation of stress-induced martensite or a phase transformation. Rather, the nickel-titanium alloy used in the strut 74 remains in its martensitic phase throughout delivery, deployment, and recovery from the body lumen.

Because of the wedging action from the beveled periphery of the key holes 76 and wide base 86, the strut 74 cannot fall through the key hole towards the interior of the tubular body 72. The wide base 86 of the strut 74 is joined to the key holes 76 by use of glue, solder, or the like. To further secure the struts 74 to the tubular body, there is an optional sleeve 90 that slides over the proximal end 82 of the tubular body thus holding the wide bases 86 inside their respective key holes. This is shown in the perspective view of FIG. 6e.

In an alternative embodiment, as seen in FIG. 6e, a tubular shape inner sleeve 94 that fits inside the tubular body 72 can be used to hold the struts 74 in place. The inner sleeve 94 as well as the outer sleeve 90 can be made from stainless steel, a rigid plastic such as polyamide, or similar material known in the art.

Also shown in FIGS. 6c and 6d are two alternative embodiments of the wide base 86 in which the curvature 88 has been reduced to the radius of the small diameter tubular body 72 thereby conforming to the surface profile. On the other hand, a wide base 92 has not been conformed into the radius of the small diameter tubular body 72. Either configuration for the wide bases 86, 92 are contemplated, with the wide base 86 having curvature 88 being the preferred design because the fitted joint involves less tolerance and the strut 74 extends from a more stable platform.

The strut 74 is either left at the large tube diameter or it may be cold and/or heat formed to the curved shape shown. Heat forming at the wide base 86 is possible even to maintain the material in the martensitic state because during delivery, deployment, and recovery, the wide base 86 does not undergo any bending. If it is left in the large tube diameter shape, it is flexed into the position shown in FIGS. 6c and 6d by the sleeve 90 pressing against the wide base 86 against the key hole 76.

Typically, the small diameter tubing is laser cut from a hypotube having a 0.026 inch diameter. It is then expanded and heat set at the fully expanded state to create the expanded strut configuration. By using parts fashioned from tubing of two different diameters as in the present invention, the need for performing an expansion and heat set are eliminated. Thus, a 4.0 mm device is cut from approximately 4.5 mm tubing, and a 5.0 mm device is cut from approximately 5.5 mm tubing, etc.

While the present invention has been illustrated and described herein in terms of linear pseudoelastic nitinol filter assembly of an embolic protection device and its delivery system, it is apparent to those skilled in the art that the present invention can be used in other instances. Other modifications and improvements may be made without departing from the scope of the present invention.

What is claimed is:

1. A medical device for use in a body lumen, comprising:
a tubular body formed from small diameter tubing;
a plurality of struts formed from a large diameter tubing and disposed on the tubular body such that the struts project radially outward in an unconstrained state;
wherein the large diameter tubing includes a cold formed nickel-titanium alloy, and the nickel-titanium alloy is in a martensitic phase only regardless of stress applied to the alloy, and wherein the tubular body has been heat treated and a hysteresis curve of the nickel-titanium alloy does not include a stress plateau; and
a sheath at least partially enveloping the body and restraining the struts in a compressed state for delivery and retrieval of the device to and from the body lumen.

2. The medical device of claim 1, wherein the strut includes a long beam extending from a wide base, and the tubular body includes apertures formed therein, and wherein each aperture receives the wide base of the strut therein.

3. The medical device of claim 2, wherein the long beam of the strut includes a sloped profile.

4. The medical device of claim 2, wherein the aperture has a beveled interior edge and the wide base has a matching beveled edge.

5. The medical device of claim 2, wherein the medical device includes a sleeve that slidably engages the tubular body and covers the wide bases of the struts thereby retaining the struts to the body.

6. The medical device of claim 1, wherein the struts assume a shape imparted by cold forming.

7. The medical device of claim 6, wherein the cold forming occurs below the recrystallization temperature of the nickel-titanium alloy.

8. The medical device of claim 1, wherein the ingot transformation temperature of the nickel-titanium alloy is set above 37 degrees C.

9. The medical device of claim 1, wherein the small diameter tubing includes a nickel-titanium alloy.

10. A medical device for delivery to, deployment within, and removal from a lumen of a mammalian body, comprising:

a tubular body derived from small diameter tubing having a plurality of apertures formed therein;

a plurality of struts derived from a large diameter tubing;

wherein the apertures receive the struts therein and in an unstressed state bend away from the tubular body;

wherein the small and large diameter tubing include a cold formed nickel-titanium alloy, and the nickel-titanium alloy is in a martensitic phase only regardless of stress applied to the alloy; and a sheath at least partially enveloping the body and restraining the struts in a compressed state for delivery and retrieval of the device to and from the lumen.

11. The medical device of claim 10, wherein the strut is cold formed to provide a curvature in a profile thereof.

12. The medical device of claim 10, wherein the strut includes a long beam extending from a wide base, and the wide base includes a radius of curvature matching a radius of curvature of the tubular body.

13. The medical device of claim 12, wherein some of the apertures have a first shape and the wide bases of the struts have a second shape complementary to the first shape so that at least a portion of the struts is recessed into the tubular body when attached thereto.

14. The medical device of claim 10, wherein the strut includes a long beam extending from a wide base, and the wide base includes a beveled periphery that wedges against a beveled periphery of the aperture.

15. The medical device of claim 10, wherein the strut has been heat treated and a hysteresis curve of the nickel-titanium alloy does not include a stress plateau.

16. The medical device of claim 10, wherein the nickel-titanium alloy has received low temperature heat treating and does not undergo a phase transformation when stressed.

17. The medical device of claim 10, wherein the struts are bonded to the tubular body.

18. A method for providing a medical device for use in a body lumen, comprising:

providing a small diameter tubing;

forming the small diameter tubing into a tubular body;

providing a large diameter tubing wherein the large diameter tubing includes a cold formed nickel-titanium alloy wherein the nickel-titanium alloy is in a martensitic phase only regardless of stress applied to the alloy;

heat treating the nickel-titanium alloy at a low temperature;

fashioning a plurality of struts from the large diameter tubing;

disposing the struts on the tubular body such that the struts project radially outward in an unconstrained state; and providing a sheath that at least partially envelopes the body and restrains the struts in a compressed state for delivery and retrieval of the device to and from the body lumen.

19. The method for providing a medical device of claim 18, wherein the method further comprises providing a small tubing including a cold formed nickel-titanium alloy wherein the nickel-titanium alloy is in a martensitic phase only regardless of stress applied to the alloy.

20. The method for providing a medical device of claim 18, wherein the strut is cold formed to achieve a curved profile.

21. A medical device for use in a body lumen, comprising:

a tubular body formed from small diameter tubing;

a plurality of struts formed from a large diameter tubing and disposed on the tubular body such that the struts project radially outward in an unconstrained state;

wherein the large diameter tubing includes a cold formed nickel-titanium alloy that includes heat treating and wherein a hysteresis curve of the nickel-titanium alloy does not include a stress plateau, and the nickel-titanium alloy is in a martensitic phase only regardless of stress applied to the alloy; and a sheath at least partially enveloping the body and restraining the struts in a compressed state for delivery and retrieval of the device to and from the body lumen.

\* \* \* \* \*

UNITED STATES PATENT AND TRADEMARK OFFICE
CERTIFICATE OF CORRECTION

PATENT NO.    : 6,551,341 B2  
DATED         : April 22, 2003  
INVENTOR(S)   : John F. Boylan et al.

It is certified that error appears in the above-identified patent and that said Letters Patent is hereby corrected as shown below:

<u>Title page,</u>
Item [56], OTHER PUBLICATIONS, change "Stöockel", to read -- Stöckel --.

Signed and Sealed this

Fifteenth Day of July, 2003

JAMES E. ROGAN
*Director of the United States Patent and Trademark Office*